US010430601B2

(12) United States Patent
Jiang (10) Patent No.: US 10,430,601 B2
(45) Date of Patent: Oct. 1, 2019

(54) AUTHORIZATION CONTROL DEVICE, SYSTEM AND SMART APPARATUS FOR CONVENIENT FOOD AND DIGITAL MENU (71) Applicant: Zhuhai Unitech Power Technology Co., Ltd., Guangdong (CN)

(72) Inventor: Haifeng Jiang, Guangdong (CN)

(73) Assignee: ZHUHAI UNICOOK TECHNOLOGY CO., LTD., Zhuhai (CN)

( * ) Notice: Subject to any disclaimer, the term of this patent is extended or adjusted under 35 U.S.C. 154(b) by 32 days.

(21) Appl. No.: 15/102,546

(22) PCT Filed: Dec. 1, 2014

(86) PCT No.: PCT/CN2014/092692
§ 371 (c)(1),
(2) Date: Jun. 8, 2016

(87) PCT Pub. No.: WO2015/085878
PCT Pub. Date: Jun. 18, 2015

(65) Prior Publication Data
US 2016/0314311 A1 Oct. 27, 2016

(30) Foreign Application Priority Data

Dec. 9, 2013 (CN) .......................... 2013 1 0664566
Dec. 9, 2013 (CN) .......................... 2013 1 0665390
Dec. 9, 2013 (CN) .......................... 2013 1 0665441

(51) Int. Cl.
*G06F 21/62* (2013.01)
*G06F 16/2455* (2019.01)
(Continued)

(52) U.S. Cl.
CPC ...... *G06F 21/6218* (2013.01); *G06F 16/2455* (2019.01); *G06F 19/3475* (2013.01);
(Continued)

(58) Field of Classification Search
CPC ........... G06F 21/6218; G06F 17/30477; G06F 21/10; G06F 21/31; G06F 21/36; G09B 19/0092
See application file for complete search history.

(56) References Cited

U.S. PATENT DOCUMENTS 7,031,946 B1    4/2006  Tamai et al.
7,523,302 B1 *  4/2009  Brown ................ G06F 21/6209
                                                      380/201
(Continued)

FOREIGN PATENT DOCUMENTS

CN    102824098 A    12/2012
CN    102853459 A    1/2013
(Continued)

OTHER PUBLICATIONS

English language abstract and machine translation for CN102824098(A) extracted from http://worldwide.espacenet.com database on Nov. 22, 2016, 7 pages.
(Continued)

*Primary Examiner* — Oleg Korsak
(74) *Attorney, Agent, or Firm* — Warner Norcross & Judd LLP (57) ABSTRACT Disclosed is an authorization control method of convenient food and a digital menu. A database stores digital menu information, convenient food specification information, digital menu instantiation information and convenient food product information. The convenient food product information and digital menu instantiation information in the database are processed so as to generate convenient food product information unit and digital menu instantiation information unit. By creating the convenient food product information and the digital menu instantiation information, the invention can manage the usage authorization of the convenient food specification information and the digital menu information,
(Continued)

while simultaneously associating the convenient food product information and the digital menu instantiation information, thus increasing the convenience in using convenient food.

12 Claims, 4 Drawing Sheets

(51) Int. Cl.

| | | |
|---|---|---|
| *G06F 21/10* | (2013.01) | |
| *G06F 21/31* | (2013.01) | |
| *G06Q 20/12* | (2012.01) | |
| *G09B 19/00* | (2006.01) | |
| *G06F 21/36* | (2013.01) | |
| *G06F 19/00* | (2018.01) | |
| *G06Q 20/20* | (2012.01) | |
| *H04W 12/00* | (2009.01) | |

(52) U.S. Cl.
CPC .............. *G06F 21/10* (2013.01); *G06F 21/31* (2013.01); *G06F 21/36* (2013.01); *G06Q 20/1235* (2013.01); *G06Q 20/203* (2013.01); *G09B 19/0092* (2013.01); *H04L 2463/101* (2013.01); *H04W 12/00522* (2019.01)

(56) References Cited

U.S. PATENT DOCUMENTS

| 2002/0026325 | A1 | | 2/2002 | Hirahara et al. | |
|---|---|---|---|---|---|
| 2003/0171944 | A1 | * | 9/2003 | Fine | ........................ G06Q 30/06 705/2 |
| 2005/0192869 | A1 | | 9/2005 | Maeda et al. | |
| 2010/0057540 | A1 | | 3/2010 | Tanaka et al. | |
| 2013/0171304 | A1 | * | 7/2013 | Huntley | .................. G06Q 50/00 426/231 |

FOREIGN PATENT DOCUMENTS

| CN | 102968579 A | 3/2013 |
|---|---|---|
| CN | 103020875 A | 4/2013 |
| CN | 103049778 A | 4/2013 |
| CN | 104111963 A | 10/2014 |
| CN | 104112087 A | 10/2014 |
| CN | 104113520 A | 10/2014 |
| EP | 1742513 A2 | 10/2007 |
| JP | 2002099601 A | 4/2002 |
| JP | 2002351876 A | 12/2002 |
| JP | 2002352029 A | 12/2002 |
| JP | 2005148850 A | 6/2005 |
| JP | 2008199633 A | 8/2008 |
| JP | 201055489 A | 3/2010 |
| JP | 2010061382 A | 3/2010 |
| JP | 2013084310 A | 5/2013 |
| WO | WO03107233 A1 | 12/2003 |

OTHER PUBLICATIONS

English language abstract and machine translation for CN102853459(A) extracted from http://worldwide.espacenet.com database on Nov. 22, 2016, 17 pages.
English language abstract and machine translation for CN103049778(A) extracted from http://worldwide.espacenet.com database on Nov. 22, 2016, 17 pages.
PCT/CN2014/092692 International Search Report dated Mar. 4, 2015, 2 pages.
English language abstract and machine translation for CN102968579(A) extracted from http://worldwide.espacenet.com database on Aug. 3, 2016, 54 pages.
English language abstract and machine translation for CN103020875 (A) extracted from http://worldwide.espacenet.com database on Aug. 3, 2016, 14 pages.
English language abstract and machine translation for CN104111963 (A) extracted from http://worldwide.espacenet.com database on Aug. 1, 2016, 32 pages.
English language abstract and machine translation for CN104113520 (A) extracted from http://worldwide.espacenet.com database on Aug. 3, 2016, 25 pages.
English language abstract and machine translation for CN104112087 (A) extracted from http://worldwide.espacenet.com database on Aug. 3, 31 pages.
English language abstract and machine translation for JP2002099601 (A) extracted from http://worldwide.espacenet.com database on Feb. 1, 2018, 12 pages.
English language abstract and machine translation for JP2002351876 (A) extracted from http://worldwide.espacenet.com database on Feb. 1, 2018, 17 pages.
English language abstract and machine translation for JP2002352029 (A) extracted from http://worldwide.espacenet.com database on Feb. 1, 2018, 16 pages.
English language abstract and machine translation for JP2005148850 (A) extracted from http://worldwide.espacenet.com database on Feb. 1, 2018, 15 pages.
English language abstract and machine translation for JP2010061382 (A) extracted from https://www.j-platpat.inpit.go.jp. database on Feb. 1, 2018, 29 pages.
English language abstract and machine translation for JP2013084310 (A) extracted from http://worldwide.espacenet.com database on Feb. 1, 2018, 17 pages.

* cited by examiner

AUTHORIZATION CONTROL DEVICE, SYSTEM AND SMART APPARATUS FOR CONVENIENT FOOD AND DIGITAL MENU

CROSS-REFERENCE TO RELATED APPLICATIONS

This application is the National Stage of International Application No. PCT/CN2014/092692, filed on 1 Dec. 2014, which claims priority to and all advantages of Chinese Patent Application No. 201310664566.X, filed on 9 Dec. 2013, Chinese Patent Application No. 201310665390.X, filed on 9 Dec. 2013, and Chinese Patent Application No. 201310665441.9, filed on 9 Dec. 2013, the content of which are hereby incorporated by reference.

TECHNICAL FIELD

The invention relates to the field of authorization control of cooking product, in particular, to an authorization control method, system and smart apparatus for convenient food and digital menu.

BACKGROUND

With the development of science and technology and the acceleration of the pace of life, there is a more and more urgent desire for people to be liberated from housework of daily meals. Therefore, "convenient food" has become a well-selling product in the shopping place or market. Convenient food, also referred as to pre-packed food or semi-finished food, is a product obtained by vacuum-packing or quick-freezing food in a sterile environment after the food has been subject to such processing operations as cleaning up (e.g., removing unusable part, splitting, or the like), washing, sterilizing and flavoring.

With the development of convenient food processing technology and information technology, a digital menu used for convenient food product has emerged as the time requires. Theoretically, a digital menu for convenient food is a cooking program having a universal standard format obtained by processing the cooking processes performed by chefs of various cooking styles on convenient food. The application of digital menu for convenient food has met cooking requirements of consumers on various convenient foods when using smart cooking appliance. That is, after the consumer has bought convenient food product, a cooking process of the convenient food can be completed automatically or semi-automatically on smart cooking appliance under the guidance of a digital menu corresponding to this convenient food product, thus greatly improving the automation level in kitchen cooking.

The digital menu is a digital product which has such characteristics as convenient movement and reproduction. Therefore, the producer of digital menu cannot manage the authorized use of digital menu like managing the ownership for conventional physical products. Based on the characteristics of digital products, the rights of digital menu producer can be really protected only if an authorization management can be conducted on each copy of the digital menu produced by the digital menu producer. Meanwhile, one of more material objects of convenient food product produced by convenient food producer according to the specification of convenient food product can be also considered as a reproduction of the specification of convenient food product. When different convenient food products are sold to different users, it can be also considered that the authorizations of these convenient food products are also transferred differently. However, there is currently no ideal solutions for the problem of how to obtain usage authorization of a matching digital menu through different convenient food products when these different convenient food products are used, or how to obtain matching convenient food product information through different digital menu instantiations when using these different digital menu instantiations for convenient food.

Moreover, during use of digital menu for convenient food, there is currently no apparatus which can supervise and manage authorizations of convenient food or digital menu effectively, i.e., to record convenient food or digital menu that has been ran/used, or to determine the legitimacy of used convenient food or digital menu.

Therefore, there is a need for an authorization control method which overcomes the authorization management problem in application of existing convenient food and digital menu; meanwhile, there is also a need for an apparatus which can conduct effective supervision and management on the authority of executed digital menu.

SUMMARY

In view of the above technical problem, the invention provides an authorization control method and an authorization control system of convenient food and digital menu, which address the problem of inconvenient usage authorization management of digital menu, and meanwhile associates convenient food product information with digital menu instantiation information, thus increasing convenience in use of convenient food; based on the above authorization control method of digital menu, the invention also provides a smart apparatus which can realize effective supervision of authorization management of convenient food and digital menu.

According to an aspect of the invention, an authorization control method of convenient food and digital menu is provided, comprising the following steps:

(1) establishing a database which stores digital menu information, convenient food specification information corresponding to the digital menu information, one or more digital menu instantiation information generated according to the digital menu information, and one or more convenient food product information generated according to the convenient food specification information;

(2) processing the convenient food product information and the digital menu instantiation information respectively so as to generate a convenient food product information unit and a digital menu instantiation information unit respectively;

(3) presetting corresponding digital menu instantiation information in the convenient food product information unit and/or presetting corresponding convenient food product information in the digital menu instantiation information unit;

(4) validating information in the convenient food product information unit, and granting usage authorization of digital menu instantiation information corresponding to the convenient food product information after the information is validated legitimate; or validating information in the digital menu instantiation information unit, and granting usage authorization of convenient food product information corresponding to the digital menu instantiation information after the information is validated legitimate.

Optionally, processing the information comprises digitally processing the convenient food product information and the digital menu instantiation information respectively so as to generate convenient food product recognition information and digital menu instantiation recognition information respectively.

Optionally, the digital menu instantiation recognition information corresponding to the convenient food product information is built in the convenient food product information unit, and/or the convenient food product recognition information corresponding to the digital menu instantiation information is built in the digital menu instantiation information unit.

Optionally, before step (3), the method further comprises: processing each convenient food specification information and each digital menu information in the database respectively so as to generate a convenient food specification information unit and a digital menu information unit respectively; wherein processing the information comprises digitally processing the convenient food specification information and the digital menu information respectively so as to generate convenient food specification recognition information and digital menu recognition information respectively.

Optionally, each of the convenient food specification recognition information, the convenient food product recognition information, the digital menu recognition information and the digital menu instantiation recognition information are character code or graphic code depicted in machine language.

Optionally, the convenient food specification information corresponds to and associates with the convenient food product information, the convenient food specification information corresponds to and associates with the digital menu information, and the digital menu information corresponds to and associates with the digital menu instantiation information.

Optionally, the associated and corresponding relationship between the convenient food specification information and the convenient food product information is a relationship in which one convenient food specification information corresponds to one or more convenient food product information; the associated and corresponding relationship is realized by embedding each of the convenient food product recognition information generated based on the convenient food specification information into the convenient food specification information unit and/or embedding the convenient food specification recognition information into each of the convenient food product information unit;

The associated and corresponding relationship between the convenient food specification information and the digital menu information is realized by embedding the digital menu recognition information corresponding to the convenient food specification information into the convenient food specification information unit and/or embedding the convenient food specification recognition information corresponding to the digital menu information into the digital menu information unit.

The associated and corresponding relationship between the digital menu information and the digital menu instantiation information is a relationship in which one digital menu information corresponds one or more digital menu instantiation information; this associated and corresponding relationship is realized by embedding each of the digital menu instantiation recognition information generated based on the digital menu information into the digital menu information unit and/or embedding the digital menu recognition information into each of the digital menu instantiation information unit.

Optionally, the validating comprises the following process:
obtaining the convenient food product information;
verifying the legitimacy of the convenient food product information;
calling out the convenient food product information unit corresponding to the convenient food product information via the convenient food product information after the convenient food product information is verified legitimate;
obtaining use authorization of the digital menu instantiation information corresponding to the convenient food product information via the convenient food product information unit;
or obtaining the digital menu instantiation information;
verifying the legitimacy of the digital menu instantiation information;
calling out the digital menu instantiation information unit corresponding to the digital menu instantiation information via the digital menu instantiation information after the digital menu instantiation information is verified legitimate;
obtaining use authorization of the convenient food product information corresponding to the digital menu instantiation information via the digital menu instantiation information unit.

Optionally, the convenient food product information is convenient food product recognition information, and the digital menu instantiation information is digital menu instantiation recognition information.

Optionally, the convenient food product information or the digital menu instantiation information is a character code or graphic code depicted in encrypted machine language.

Optionally, the use authorization of the digital menu instantiation information comprises partial or entire limitations on the times of downloading/using, the scope of downloading/using and the term of downloading/using the digital menu instantiation information.

Optionally, the use authorization of the convenient food product information comprises partial or entire limitations on the scope of downloading/using and the term of downloading/using the convenient food product information.

Optionally, the digital menu instantiation information and the convenient food product information are generated automatically or generated upon user's request.

According to another aspect of the invention, an authorization control system of convenient food and digital menu is further provided, and the authorization control system comprises a convenient food product information management unit, a digital menu instantiation information management unit and a database, wherein the convenient food product information management unit performs information processing on the convenient food product information in the database so as to generate a convenient food product information unit;

the digital menu instantiation information management unit performs information processing on the digital menu instantiation information in the database so as to generate a digital menu instantiation information unit;

the digital menu instantiation information corresponding to the convenient food product information unit is preset in the convenient food product information unit, and/or the convenient food product information corresponding to the digital menu instantiation information unit is preset in the digital menu instantiation information unit;

the authorization control system conducts validation based on information in the convenient food product information unit, and after the information is validated legitimate, grants usage authorization of the digital menu instantiation information corresponding to the convenient food product information; or the authorization control system conducts validation based on information in the digital menu instantiation information unit, and after the information is validated legitimate, grants usage authorization of the convenient food product information corresponding to the digital menu instantiation information.

Optionally, the digital menu instantiation information management unit further comprises an encrypting module which performs encrypting processing on the digital menu instantiation information.

According to further another aspect of the invention, a smart apparatus is further provided, which comprises a control module, a communication module and a power supply module, wherein the control module is connected to the communication module, the control module and the communication module are connected to the power supply module respectively, and the smart apparatus obtains usage authorization of digital menu instantiation information corresponding to the convenient food product information via the convenient food product information, or the smart apparatus obtains usage authorization of convenient food product information corresponding to the digital menu instantiation information via the digital menu instantiation information, wherein, the communication module receives convenient food product recognition information and/or digital menu instantiation recognition information and sends them to the control module, wherein the convenient food product recognition information and the digital menu instantiation recognition information are obtained by processing the convenient food product information and the digital menu instantiation information respectively;

the control module determines a correspondence relationship of the convenient food product recognition information and the digital menu instantiation recognition information;

and after the information is validated legitimate, the smart apparatus obtains the right to resolve and execute the digital menu instantiation information, or obtains usage authorization of convenient food product information corresponding to the digital menu instantiation information.

Optionally, the convenient food product recognition information and the digital menu instantiation recognition information are obtained by via user's account information and/or smart apparatus information.

Optionally, the control module further comprises a decrypting module; after the decrypting module decrypts the digital menu instantiation information, the smart apparatus obtains the right to resolve and execute the digital menu instantiation information.

Optionally, the resolved digital menu instantiation information is sent to an execution module to be executed; the execution module is disposed inside the smart apparatus, or disposed on one or more smart cooking appliance outside the smart apparatus.

Optionally, the smart apparatus comprises a database which stores convenient food product information and digital menu instantiation information; according to the information in the database, the control module directly determines a correspondence relationship of the convenient food product recognition information and the digital menu instantiation recognition information.

Optionally, the control module indirectly determines a correspondence relationship of the convenient food product recognition information and the digital menu instantiation recognition information via a management server, wherein the management server is an integrated management server for convenient food and digital menu, or independent convenient food management server and digital menu management server respectively.

Optionally, the smart apparatus has direct access to the management server via the communication module, or the smart apparatus has indirect access to the management server via an intermediate apparatus.

Optionally, the smart apparatus further comprises an encrypting module which performs encryption processing on information sent by the smart apparatus to the management server that needs to be kept secret.

Optionally, the smart apparatus further comprises a non-volatile memory module, and the smart apparatus stores a use record of the digital menu instantiation information in the memory module; after the smart apparatus and the management server are communicatively connected, the use record information is actively or passively uploaded to the management server.

Optionally, the use record comprises user's information, date of use, apparatus used, the times of downloading and using, process in use or evaluation of use.

Optionally, the smart apparatus comprises a personal mobile terminal, a computer or a smart cooking appliance.

The invention brings about the following advantageous effects:

In the authorization control method of convenient food and digital menu provided by the invention, each copy of digital menu is managed in an instantiated concept, that is, each copy of digital menu is considered as a digital menu instantiation. An authorization management of digital menu is realized through an authorization management of digital menu instantiation information, and the problem of inconvenient usage authorization management caused by the fact that the digital menu is easy to reproduce and transfer is solved.

In the authorization control method of convenient food and digital menu provided by the invention, the convenient food product information and the digital menu instantiation information are associated; that is, by transmitting digital menu instantiation information via convenient food product, the owner of convenient food product can obtain corresponding digital menu instantiation information at the same time of obtaining convenient food product, or the owner of digital menu instantiation can obtain use authorization of a corresponding convenient food product, thus increasing the convenience in the use of convenient food in smart cooking system.

The management server for convenient food and digital menu provided by the invention can conduct authorized management on each reproduction of the convenient food and digital menu, and collectively records and controls the use of convenient food product information and digital menu instantiation information. Therefore, not only the menu producer is facilitated in releasing the produced digital menu, but also the consumers of digital menu are facilitated in downloading digital menu, thus ensuring the validity of authorized management of digital menu instantiation information.

The smart apparatus provided by the invention can resolve and execute convenient food or digital menu instantiation information, and meanwhile records running and usage information of convenient food product information or digital menu instantiation information, determines the legitimacy of the use of convenient food product information or digital menu instantiation information, thus realizing an effective supervision on the authorization management of convenient food and digital menu.

The smart apparatus provided by the invention can be communicatively connected to the management server, and actively or passively transmit the usage information of digital menu instantiation information to the management server so as to be recorded by the management server. In this way, it is ensured that the digital menu instantiation information will not be executed repeatedly in a network scope, and the validity of authorized usage authorization management on the digital menu resolving apparatus by the management server is ensured.

DETAILED DESCRIPTION OF THE EMBODIMENTS

The invention will be described in detail by way of the following embodiments. However, those skilled in the art will understand that the following embodiments do not serve to limit the scope of protection of the invention. Any modification and change made on the basis of the invention will fall within the scope of protection of the invention.

Figure 1:
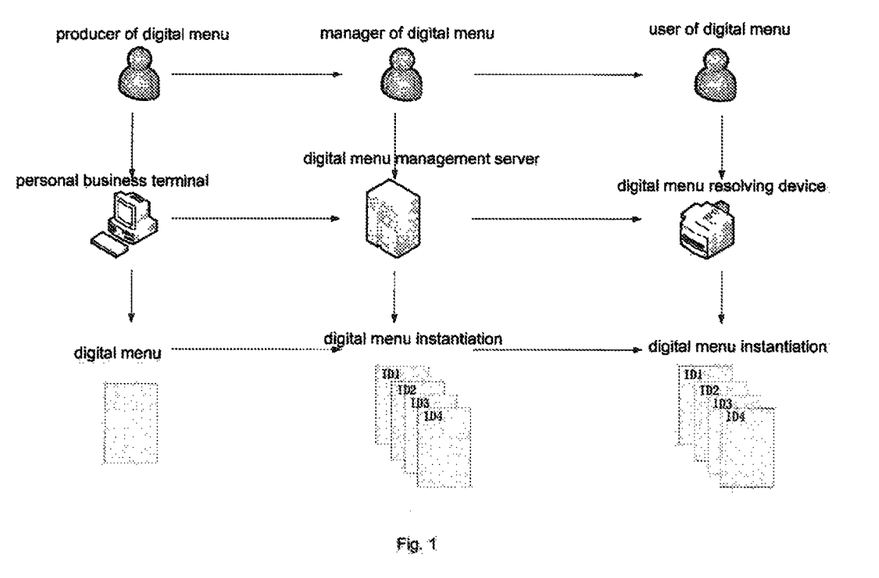
FIG. 1 is a schematic application diagram of digital menu instantiation information.

As shown in FIG. 1, which is a schematic application diagram of digital menu instantiation information, the producer of digital menu accomplishes the creation of digital menu through a personal mobile terminal or on a digital menu creating terminal. Then, the producer of digital menu uploads the created digital menu information to a digital menu management server through the personal mobile terminal or the digital menu creating terminal. The manager of digital menu sets a usage authorization of digital menu instantiation information through the digital menu management server. After obtaining the digital menu instantiation information on the digital menu management server, the user resolves the digital menu instantiation information via a digital menu resolving apparatus, and runs the digital menu instantiation information on a smart cooking appliance, thus completing smart cooking. Herein, the user obtains the digital menu instantiation information in a process in which relevant information attached in the purchased convenient food product information is uploaded to the digital menu management server, and the digital menu instantiation information and a corresponding usage authorization is obtained after the information is validated by the server.

Specifically, the producer of digital menu uploads a special digital menu to the digital menu management server. The digital menu is designed for special convenient food specification information. Therefore, in the food material information of the digital menu information, it is not the category and weight of a specific food material that are included; rather, it is convenient food specification information that is included. Assuming that the convenient food specification is a bag of various food materials that are packed in bags and identified uniformly, the food material information of the digital menu information comprises information of corresponding food material bags. The food material information in the digital menu information can be added directly by the producer of digital menu when uploading the menu, or can be automatically added by the digital menu management server when the producer of digital menu files a request with the digital menu management server after a convenient food that satisfies requirements is produced by the producer of digital menu after the digital menu is released.

Figure 2:
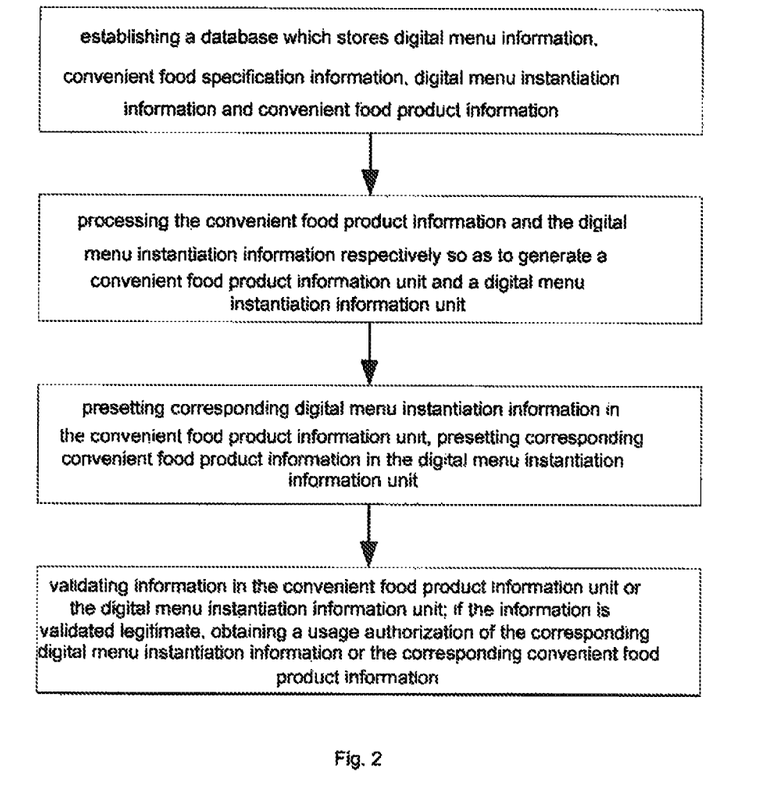
FIG. 2 is a schematic flowchart of authorization management of convenient food and digital menu.

As shown in FIG. 2, which is a schematic flowchart of authorization management of convenient food and digital menu, the flowchart comprises the following steps:

(1) building a database, wherein the database stores digital menu information, convenient food specification information corresponding to the digital menu information, one or more digital menu instantiation information generated according to the digital menu information, and one or more convenient food product information generated according to the convenient food specification information.

Specifically, the producer of digital menu uploads the produced digital menu information to the database. Optionally, a description document of the digital menu information is also uploaded simultaneously. The description document covers all the basic information of the digital menu information, wherein the description document of the digital menu information can comprise one or more of producer's information, name information, cooking style information, flavor information, food material information, food taboo information, nutrition information of the digital menu information. Specifically, the producer's information shows the information of the chef which produced this digital menu, including the name, working experience and qualification or the like of the chef; the name information can distinguish different convenient foods from each other, e.g., Kungpao Chicken, Mapo Tofu, Twice Cooked Pork, Boiled Fish, etc; the cooking style information shows the category to which the convenient food belongs, e.g., Sichuan cuisine, Shandong cuisine, Huaiyang cuisine, Guangdong cuisine, Western style food, Hunan cuisine, etc.; the flavor information comprises sour, sweet, bitter, spicy, salty, fresh, etc.; the food material information can comprise the name and weight of various food materials required for cooking this convenient food, or convenient food specification information; the food taboo information comprises the population range for which this convenient food is not suitable, e.g., pregnant woman, patients with elevated blood pressure, diabetic patients, etc, or can also comprise information of foods that are not adapted to be taken at the same time with this convenient food, e.g., it is inappropriate to take eggs together with sweeteners; the nutrition information comprises information such as analysis of nutrition compositions, calories information and traditional Chinese medicine analysis of the convenient food, etc. Preferably, the nutrition information can further comprise some regimen information, such as health protection information, cosmetology information, food therapy information, etc. Optionally, based on the information, the user can obtain a digital menu that suits him/her well, wherein some of the information such as the food taboo information or the nutrition information can be also input in a subsequent process by a third-party service authority. Whether the information is provided by the producer or by a third-party service authority, it should be released to the user only after being verified by the manager of digital menu, thus preventing the use of digital menu from being misguided by wrong information.

Specifically, when the producer of convenient food makes the convenient food, the generated convenient food specification information is uploaded to a database, or the convenient food specification information to be generated is stored in a database in advance. The convenient food specification information stored of the producer of convenient food can comprise some or all of the name information, cooking style information, flavor information, food material information, raw material producing area information, supply scope information, quality guarantee period information, food taboo information and nutrition information of the convenient food, wherein the name information, cooking style information, flavor information of the convenient food can be used by the user to search for the types of convenient food that suit him/her; since the convenient food is a fresh food, the place of origin of raw materials not only has an influence on the flavor of convenient food, but also has an influence on the supply scope of convenient food. Therefore, the convenient food specification information can comprise the raw material producing area information; meanwhile, the supply scope information can also be provided for user's choice according to the place of origin and the quality guarantee period of convenient food. The food taboo information and nutrition information in the convenient food specification information can be provided by the producer of the convenient food, or can be provided by a third-party service authority.

Specifically, one or more specific convenient food products can be produced according to any of the convenient food specification information. For example, according to the convenient food specification information, an authorized producer of convenient food can produce one or more specific convenient food products for any convenient food. The producer of the convenient food uploads the produced convenient food product information to the database, or before the producer of the convenient food produces the convenient food product, stores the convenient food product information in the database in advance, wherein the convenient food product refers to the produced physical convenient food, and the convenient food product information refers to relevant information of the physical convenient food, including the convenient food specification information and production information of the physical convenient food product, etc.

Specifically, one or more digital menu instantiation information can be generated according to any of the digital menu information. For example, assuming that the generation of digital menu instantiation information is initiated by the producer of the convenient food, the producer of the convenient food uses an authorized account to log in the digital menu management server according to the convenient food product information generated or to be generated, and requests for digital menu information corresponding to the convenient food product information with the digital menu management server. After the digital menu management server verifies the account identity of the producer of the convenient food to be qualified, digital menu instantiation information which has a corresponding number to the convenient food product information is generated according to the requested digital menu information.

The acquisition of the authorized account of the producer of convenient food can be done by subscribing. After the producer has successfully subscribed the use authorization of certain one or more digital menu information, the manager of the digital menu management server opens an account for the user, and records the information on the account's authorized use of the digital menu information in the digital menu management server. After the above authorized account is acquired, the manager of the digital menu management server can also open an account directly in the digital menu management server, and as described above, makes remarks on the authorization information of this account in the digital menu management server, and records the information on the account's authorized use of the digital menu information in the digital menu management server. Typically, the usage authorization information is provided in a corresponding database as a dedicated information unit, or directly provided in the basic information of the digital menu information.

The usage authorization information of the authorized account of the producer of convenient food comprises which digital menu information in the digital menu management server can be used by this account, what is the extent of the usage right, the term of usage, the scope of usage, etc., for example, a certain convenient food producer owns a usage right of using a certain digital menu information for 1000 time, meaning that he/she owns 1000 usage rights of the digital menu instantiation information; the term of usage defines the final date of use of the digital menu information; the scope of usage comprises the digital menu information can be used only by the producer himself or the producer can allow other producers of convenient food to use the digital menu information within his scope of usage authorization.

When the digital menu instantiation information management unit generates the digital menu instantiation information, it firstly extracts relevant information from the above convenient food product information, which comprises digital menu information corresponding to this batch of convenient food product information, the number of convenient food product information, the date of production, the information of producer, etc., and compares the relevant information with usage authorization information of the account of producer of convenient food in the digital menu management server so as to determine whether the convenient food product information generated by the producer of convenient food exceeds the scope of usage authorization.

Generally speaking, such a situation may easily occur, in which the times of using certain digital menu information exceeds the scope of usage. For example, the usage authorization of the account is a usage authorization having only 1000 digital menu instantiation information, i.e., only 1000 convenient food product information can be generated, whereas the producer of convenient food generates 2000 or even more convenient food product information. The convenient food product information beyond the usage authorization will not be assigned digital menu instantiation information since it exceeds the scope of authorization. The consumer, after purchasing such convenient food product information, will also be not able to use corresponding digital menu information for cooking since such convenient food product information has no corresponding digital menu instantiation information. In such a situation, the producer of convenient food can file a request with the digital menu management server so as to increase the usage authorization of his/her account.

If the scope of usage authorization is not exceeded, the digital menu instantiation information management unit assigns digital menu instantiation information for each convenient food product information. The activity that the producer of convenient food requests for digital menu instantiation information will be automatically recorded into a generation reason of a set of digital menu instantiation information by the digital menu management server. Using this information, the digital menu management server can monitor the use of digital menu instantiation information requested by the producer of convenient food.

The generated digital menu instantiation information and convenient food product information are stored in the database. Preferably, the database can further comprise a convenient food database and a digital menu database, wherein the convenient food database is used for storing convenient food specification information and convenient food product information, and the digital menu database is used for storing digital menu information and digital menu instantiation information.

In practical use, the digital menu instantiation information and the convenient food product information can be automatically generated, or can be generated upon user's request.

(2) performing information processing on the convenient food product information and the digital menu instantiation information respectively so as to generate a convenient food product information unit and a digital menu instantiation information unit respectively.

Specifically, the information processing performed on the convenient food product information means digitally processing the convenient food product information so as to generate convenient food product recognition information. Optionally, the basic information for generating the convenient food product information is collected simultaneously.

The convenient food product information management unit generates recognition information for each convenient food product information. The convenient food product recognition information is a character code or graphic code that can be depicted or recognized in machine language, wherein the character code is a full number code, or can be a full letter code, or can be a combination of letter and number; the graphic code is a 1-dimensional bar code or 2-dimensional matrix code. The convenient food product recognition information can uniquely represent a certain convenient food physical food. For example, the code of certain convenient food Kungpao Chicken is cpgbjd, or the code of certain convenient food Mapo Tofu is 80130225003. Different convenient foods can be distinguished from each other through different codes. Preferably, a mixed code of letter and number can be used inside the server so as to characterize the convenient food product information, wherein the letter can represent complicated information, such as the producer of convenient food, cooking style, etc., whereas the number can represent simple serial number information, for example, the convenient food Braised Eggplant can be characterized by code MCAK051008. Preferably, when the convenient food specification information can be also characterized by convenient food specification recognition information, the convenient food product recognition information can comprise convenient food specification recognition information in its composition. That is, by expanding the convenient food specification recognition information appropriately, the convenient food product information corresponding to this convenient food specification information can be characterized. For example, for convenient food specification recognition information MCAK051, the 829$^{th}$ convenient food product information thereof can be characterized by recognition information MCAK051000829.

At the same time of performing information processing on convenient food product information so as to obtain convenient food product specification information, optionally, the convenient food product information management unit further processes relevant information in the convenient food product information, i.e., collecting basic information for generating the convenient food product information to constitute a set of convenient food product information. The relevant information collected in the set of convenient food product information can comprise all or part of the information in the convenient food specification information and convenient food product recognition information, digital menu instantiation recognition information, or personalized information relevant to the convenient food product information, such as information of producer, date of production, batch of production, total number of production, serial number of production, etc., wherein the information type corresponding to the convenient food specification information and the information type corresponding to the convenient food product information can be interchanged, and the basis for categorizing merely depends on whether the convenient food product information belonging to the same convenient food product specification has different attributes. For example, convenient food product information generated from the same convenient food product specification may have different producing areas, and therefore producing area information can be added in the convenient food product information. If the producing areas of convenient food product information generated from the same convenient food product specification are the same, the producing area information will only have to be embodied in the set of convenient food specification information, and relevant information can be obtained simply by including the set of convenient food specification information in the set of convenient food product information.

The convenient food product recognition information for characterizing convenient food product information is stored in the convenient food product information unit of the database. Preferably, the basic information of the convenient food product information and the convenient food product recognition information are stored in the convenient food product information unit of the database together, and the basic information of the convenient food product information corresponds to and associates with the convenient food product recognition information. If only the convenient food product recognition information is known, all the basic information of the convenient food product information can be obtained.

Specifically, the information processing performed on each digital menu instantiation information by the digital menu instantiation information management unit means digitally processing each digital menu instantiation information so as to generate digital menu instantiation recognition information. The digital menu instantiation recognition information is also a character code or graphic code that can be depicted or recognized in machine language. For example, the recognition information can be a code. Specifically, it can be a full number code, e.g., 0103468749, or can be a full letter code, e.g., hongshaoqiezi, or a mixed code of number and letter, e.g., Menu7623500127. The only restriction condition of the form of recognition information is that it can be depicted in machine language. Therefore, the recognition information can not only be embodied as character code, but also can be embodied as graphic code, e.g., 1-dimensional bar code or 2-dimensioanl matrix code. The digital menu instantiation information after being digitally processed has a unique ID (i.e., digital menu instantiation recognition information) in the whole database, or even in the application system of the digital menu instantiation information. Preferably, when the digital menu information is also characterized by the digital menu recognition information, the digital menu instantiation recognition information can comprise digital menu recognition information in its composition. That is, by expanding the digital menu recognition information appropriately, the digital menu instantiation information corresponding to this digital menu information can be characterized. For example, for digital menu recognition information HSQZ025, the $800^{th}$ digital menu instantiation information thereof can be characterized by recognition information HSQZ025000800.

At the same time of performing information processing on digital menu instantiation information so as to obtain digital menu instantiation recognition information, optionally, the digital menu instantiation information management unit further processes relevant information in the digital menu instantiation information, i.e., collecting basic information for generating the digital menu instantiation information to constitute a set of digital menu instantiation information. The relevant information collected in the set of digital menu instantiation information can comprise all or part of the information in the digital menu information and convenient food product recognition information, digital menu instantiation recognition information, user's information, the generation time of digital menu instantiation information, cause of generation, all or part of the information in the generation batch. The generation time can be the system time, the cause of generation can be "purchase-by-user". In case of batch production, the generation batch and the serial number in the batch can be used, and the generated total serial number is used to record the total instantiation generation serial number of the digital menu.

In addition, in the basic information of digital menu instantiation information, there is also information reflecting a usage authorization of the digital menu instantiation information by corresponding convenient food product information. The usage authorization information comprises the following: based on the convenient food product information, the user is limited in some or all the authorizations of the times of downloading/using, the scope of downloading/using and the term of downloading/using the corresponding digital menu instantiation information, wherein the number of times of downloading/using one digital menu instantiation information is typically one. If an abnormality is found, e.g., repeated use or multiple times of use, alarming information will be provided automatically; the scope of downloading/using indicates the scope of users who can download/use the digital menu instantiation information. The user typically covers individuals, business places or smart apparatuses. When it is determined that a certain user is not in the scope of downloading/using, it means that this user has no authorization to download/use the digital menu information, and alarming information will also be provided.

In order to record ownership of the usage authorization of the digital menu instantiation information, certain personal information of the user and the digital menu instantiation information can be bonded, i.e., certain personal information of the user is recorded a set of information corresponding to the digital menu instantiation information. The personal information of user can be a register name on the digital menu management server or other associated information, such as cell phone number, identity number, email box or other information that can characterize personal features. If the user completes downloading of digital menu information by logging in the digital menu management server by resolving and running the smart cooking apparatus of the digital menu information, the unique recognition information of the smart cooking apparatus can be also recorded in a set of information corresponding to the digital menu instantiation information so as to indicate the ownership of the usage authorization of the digital menu instantiation information. According to different IDs, different authorization levels can be set. For example, the different authorization levels can comprise looking up part of the digital menu information, or looking up all the digital menu information, or looking up and downloading part of the digital menu information, or looking up and downloading all the digital menu information, or modifying the usage authorization of some accounts in the database, updating corresponding user's ID information of some accounts, or modifying the usage authorization of all the accounts in the database, and updating corresponding user's ID information of all the accounts, etc.

The digital menu instantiation recognition information is stored in the digital menu instantiation information unit of the database. Preferably, the basic information of the digital menu instantiation information and the digital menu instantiation recognition information are stored in the digital menu instantiation information unit of the database together. The digital menu instantiation recognition information and the digital menu instantiation information stored in the database correspond to and associate with each other.

(3) presetting digital menu instantiation information corresponding to the convenient food product information unit in the convenient food product information unit and/or presetting convenient food product information corresponding to the digital menu instantiation information unit in the digital menu instantiation information unit.

Specifically, the associated and corresponding relationship between the digital menu instantiation information and the convenient food product information is realized by embedding digital menu instantiation recognition information corresponding to the convenient food product information in the convenient food product information unit and/or embedding convenient food product recognition information corresponding to the digital menu instantiation information in the digital menu instantiation information unit.

In practical use, after the producer of convenient food obtains relevant information of the digital menu instantiation information, typically, the relevant information is included on the product package of the convenient food product or inside the package so that the usage authorization of the digital menu information is transferred to the user of the convenient food product. The user of the convenient food product downloads corresponding digital menu instantiation information from the server according to the relevant information of the digital menu instantiation information transferred from the convenient food product. Preferably, the relevant information of the digital menu instantiation information is typically the digital menu instantiation recognition information, i.e., the producer of convenient food includes the obtained digital menu instantiation recognition information onto the product package of the convenient food product or inside the package, and transfers the usage authorization of the digital menu information to the user of the convenient food product; the producer of convenient food may also download the digital menu instantiation information from the server at the same time of obtaining the digital menu instantiation recognition information, and transmits the digital menu instantiation information and the digital menu instantiation recognition information together to the user of the convenient food via the convenient food product. Alternatively, the user of the digital menu information can also obtain the usage authorization of the convenient food product corresponding to the digital menu instantiation information by purchasing and downloading the digital menu instantiation information.

(4) validating information in the convenient food product information unit, and granting usage authorization of digital menu instantiation information corresponding to the convenient food product information after the information is validated legitimate; or validating information in the digital menu instantiation information unit, and granting usage authorization of convenient food product information corresponding to the digital menu instantiation information after the information is validated legitimate.

Preferably, the following process is performed to conduct validating: obtaining convenient food product information, uploading the convenient food product information to the convenient food and digital menu management server which further verifies the legitimacy of the convenient food product information; after the convenient food product information is validated legitimate, the convenient food product information unit corresponding to the convenient food product information is called out via the convenient food product information, and the usage authorization of the digital menu instantiation information corresponding to the convenient food product information is obtained via the convenient food product information unit, wherein the determination of the legitimacy of the convenient food product information means determining whether there is corresponding convenient food product information in the server.

Alternatively: obtaining digital menu instantiation information, uploading the digital menu instantiation information to the convenient food and digital menu management server which further verifies the legitimacy of the digital menu instantiation information; after the digital menu instantiation information is validated legitimate, the digital menu instantiation information unit corresponding to the digital menu instantiation information is called out via the digital menu instantiation information, and the usage authorization of the convenient food product information corresponding to the digital menu instantiation information is obtained via the digital menu instantiation information unit, wherein the determination of the legitimacy of the digital menu instantiation information means determining whether there is corresponding digital menu instantiation information in the server;

Specifically, the usage authorization of digital menu instantiation information comprises limiting some or all of the times of downloading/using, the scope of downloading/using and the term of downloading/using the digital menu instantiation information. The usage authorization of convenient food product information comprises limiting some or all of the scope of downloading/using and the term of downloading/using the convenient food product information.

Preferably, the convenient food product information is convenient food product recognition information, and the digital menu instantiation information is digital menu instantiation recognition information.

More preferably, the digital menu product information and the digital menu instantiation information are character code or graphic code depicted in encrypted machine language.

Preferably, before step (3), the process further comprises: processing each convenient food specification information and each digital menu information in the database respectively so as to generate a convenient food specification information unit and a digital menu information unit respectively; wherein processing the information comprises digitally processing the convenient food specification information and the digital menu information respectively so as to generate convenient food specification recognition information and digital menu recognition information respectively; meanwhile, optionally, the basic information for generating the convenient food specification information and the basic information for generating the digital menu information can be collected.

Specifically, according to the convenient food specification information uploaded by the producer of convenient food, the convenient food specification information management unit will automatically generate a set of recognition information for characterizing the convenient food specification information, which is called convenient food specification recognition information. For example, the convenient food specification recognition information can be a code, and more specifically, a character code or graphic code that can be depicted or recognized by machine language. The convenient food specification recognition information can uniquely represent a certain convenient food specification. For example, the code of convenient food Kungpao Chicken is fbcgbjd, or the code of convenient food Mapo Tofu is 30225003. Different convenient food specifications can be distinguished from each other through different codes. Preferably, a mixed code of letter and number can be used inside the server so as to characterize the convenient food specification, wherein the letter can represent complicated information, such as the producer of convenient food, cooking style, etc., whereas the number can represent simple serial number information, for example, the convenient food Braised Eggplant can be characterized by code MCAK051.

Optionally, at the same time of processing the convenient food specification information so as to obtain the convenient food specification recognition information, the convenient food specification information management unit can also process the convenient food specification information uploaded from the producer of convenient food or a third-party service authority to the convenient food database, that is, to extract part or all of the information in the convenient food specification information or some information automatically generated by the convenient food specification information management unit such as the convenient food specification recognition information so as to constitute the basic information of convenient food specification information, which basic information constitutes a set of convenient food specification information.

The convenient food specification recognition information for characterizing convenient food specification information is stored in the convenient food specification information unit of the database. Preferably, the basic information of the convenient food specification information and the convenient food specification recognition information for characterizing convenient food specification information are stored in the convenient food specification information unit of the database together, and the basic information of the convenient food specification information corresponds to and associates with the convenient food specification recognition information. That is, the convenient food specification recognition information is equivalent to an index of the basic information of the convenient food specification information in the database. If only the convenient food specification recognition information is known, all the basic information of the convenient food specification information can be obtained. All the information that are relevant to the convenient food specification information obtained by the control system can be collected into a set of convenient food specification information in the database indexed by the convenient food recognition information.

Specifically, according to the digital menu information uploaded to the database and a description document of the digital menu information, the digital menu information management unit processes the digital menu information. Such information processing comprises digitally processing the digital menu information so as to generate digital menu recognition information; optionally, the basic information for generating the digital menu information is collected simultaneously.

The digital processing of digital menu information means that the digital menu information management unit automatically generates recognition information according to a given rule. For example, the recognition information can be a code. Specifically, it can be a full number code, or a full letter code, or a mixed code of number and letter. The only restriction condition of the form of recognition information is that it can be depicted in machine language. Therefore, the recognition information can not only be embodied as character code, but also can be embodied as graphic code, e.g., 1-dimensional bar code or 2-dimensioanl matrix code. The digital menu instantiation information after being digitally processed has a unique ID (i.e., digital menu instantiation recognition information) in the whole database, or even in the application system of the digital menu information.

At the same time of obtaining the recognition information by processing the digital menu information, optionally, the digital menu information management unit further processes the description document of the digital menu information uploaded to the server, i.e., to extract part or all of the information in the description document, or the digital menu information management unit automatically generates some information, such as the date of uploading the digital menu information, the recognition information of digital menu information, etc. The basic information for constituting the digital menu information is a set of digital menu information.

The digital menu instantiation recognition information for characterizing the digital menu information is stored in the digital menu information unit of the database. Preferably, the basic information of the digital menu information and the digital menu instantiation recognition information are stored in the digital menu information unit of the database together. The digital menu recognition information and the basic information of digital menu information stored in the database correspond to and associate with each other. Through various information terminals such as computer, various types of hand-held electronic terminal devices, smart cooking appliances, the user can search for or look up the digital menu information via various keywords. For example, the recognition information of the digital menu information can be input directly so as to conduct accurate search; also, the name, cooking style or the like of the digital menu information can be input so as to look up certain kind of food. Typically, in the process of searching or looking up, the digital menu information management server conducts searching in the basic information of various digital menu information based on the input keywords so as to match corresponding digital menu information.

All the basic information of the digital menu information in the data base, including the recognition information, is not only stored in the database of the local server, but also can be released to the network through a WEB service function of the digital menu management server so that users can browse, look up and search. Through looking up and searching for the digital menu information, the digital menu management server can also automatically position a convenient food corresponding to the digital menu information for users, thus providing maximal convenience for users in picking up convenient food.

In order to prevent the sever from being invaded illegally so that the data of digital menu information in the database is obtained and used illegally, the digital menu information stored in the database of local server can exist in an digitally encrypted form after being encrypted. The encrypting method can use a universal encrypting algorithm, such as DES, RSA, DSA, etc., or can use a certain private algorithm Preferably, the convenient food specification information, the convenient food product information, the digital menu information and the digital menu instantiation information are associated with each other, comprising: the convenient food specification information corresponds to and associates with the convenient food product information, the convenient food specification information corresponds to and associates with the digital menu information, and the digital menu information corresponds to and associates with the digital menu instantiation information. Specifically, the associated and corresponding relationship between the convenient food specification information and the convenient food product information shows that one convenient food specification information corresponds to one or more convenient food product information, and is realized by embedding each of the convenient food product recognition information generated based on the convenient food specification information into the convenient food specification information unit and/or embedding the convenient food specification recognition information into each of the convenient food product information unit. The associated and corresponding relationship between the convenient food specification information and the digital menu information is realized by embedding the digital menu recognition information corresponding to the convenient food specification information into the convenient food specification information unit and/or embedding the convenient food specification recognition information corresponding to the digital menu information into the digital menu information unit. It is worth noting that one kind of convenient food specification information can have many kinds of digital menu information. The associated and corresponding relationship between the digital menu information and the digital menu instantiation information is a relationship in which one digital menu information corresponds one or more digital menu instantiation information, and is realized by embedding each of the digital menu instantiation recognition information generated based on the digital menu information into the digital menu information unit and/or embedding the digital menu recognition information into each of the digital menu instantiation information unit. In practical use, after purchasing the convenient food product, the user obtains convenient food product information attached in the convenient food product, for example, comprising convenient food product recognition information or digital menu instantiation recognition information, etc. According to the convenient food product information, the owner of the convenient food product information accesses the convenient food and digital menu management server through a personal mobile terminal such as personal computer, cell phone or tablet computer, or through computer, smart cooking appliance, etc. The obtained convenient food product information is uploaded to the server which verifies the legitimacy of the convenient food product information; after the convenient food product information is verified legitimate, the owner of the convenient food product can obtain a usage authorization of the digital menu instantiation information corresponding to the convenient food product. That is, he/she can download the digital menu instantiation information to the smart apparatus which resolves the digital menu instantiation information, thus conducting automatic or semi-automatic cooking using the digital menu instantiation information.

The relevant information of convenient food product information, such as convenient food product recognition information or other recognition information that can represent the uniqueness of the convenient food product information, comprises the digital menu instantiation recognition information, which is sent to the consumers in a form of commodity via the convenient food product information. The relevant information can be attached on the product package of the convenient food product or inside the package.

In order to prevent the above relevant information of the convenient food product information from being leaked abnormally, the above relevant information of the convenient food product information can be encrypted. For example, a plain text code is replaced with an encrypted character and graphic code; or the relevant information of the convenient food product information can be protected by being covered with scrapable ink. After purchasing the convenient food product, the user obtains relevant information of the convenient food product information included in the convenient food product package, and also owns the usage authorization of corresponding digital menu instantiation information. According to different ways of protecting the relevant information of the convenient food product information, the user can directly read the relevant information of the convenient food product information, or obtain the relevant information of the convenient food product information by restoring from the encrypted character code and graphic code by scraping the ink coverage or by using a decrypting device, or by a combination of the above two ways. Preferably, a bar code or a matrix code comprising the above mixed codes can be used to characterize the convenient food product information, since the bar code or matrix code has a certain secret keeping function and a characteristic of convenient interchanged use.

In practical use, the user can also purchase and download the digital menu instantiation information, and according to the digital menu instantiation information, further obtains a usage authorization of a corresponding convenient food product without the need for purchasing the convenient food product again, thus increasing the convenience for users.

Figure 3:
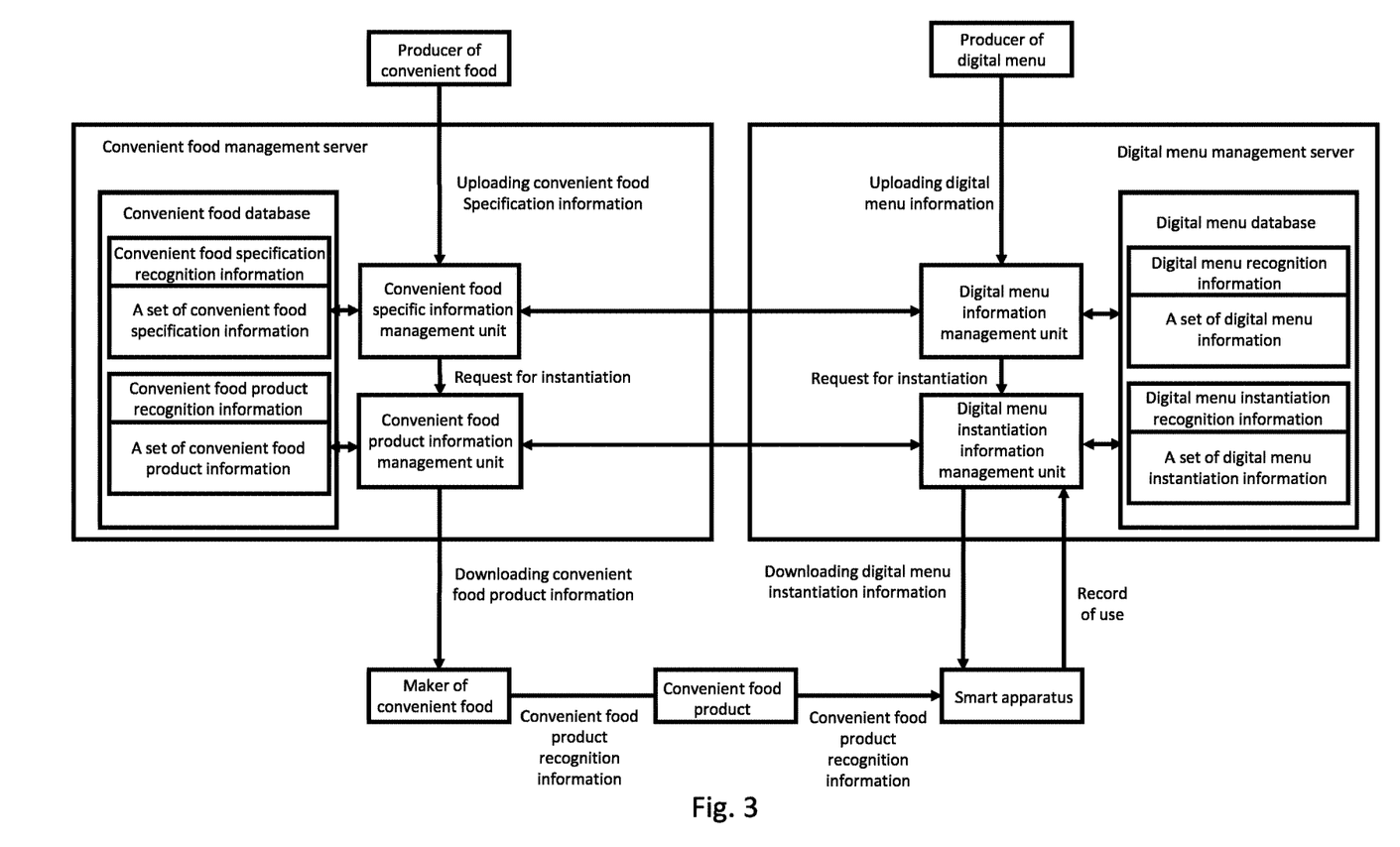
FIG. 3 is a schematic diagram showing the module components of an authorization control system of convenient food and digital menu.

As shown in FIG. 3, which is a schematic diagram showing the module components of an authorization control system of convenient food and digital menu according to the invention, the authorization control system can specifically comprise a convenient food and digital menu management server, or can comprise a convenient food management server and a digital menu management server respectively. Preferably, the present embodiment uses a convenient food management server and a digital menu management server, wherein the convenient food management server comprises a convenient food product information management unit and a convenient food database; and the digital menu management server comprises a digital menu instantiation information management unit and a digital menu database.

Specifically, the convenient food product information management unit processes the convenient food product information in the convenient food database so as to generate a convenient food information unit, and the digital menu instantiation information management unit processes the digital menu instantiation information in the digital menu database so as to generate a digital menu instantiation information unit.

The digital menu instantiation information corresponding to the convenient food product information unit is preset in the convenient food product information unit, and/or the convenient food product information corresponding to the digital menu instantiation information unit is preset in the digital menu instantiation information unit.

The authorization control system conducts validation based on information in the convenient food product information unit, and after the information is validated legitimate, the owner of the convenient food product information obtains a usage authorization of the digital menu instantiation information corresponding to the convenient food product information; or the authorization control system conducts validation based on information in the digital menu instantiation information unit, and after the information is validated legitimate, the owner of the digital menu instantiation information obtains a usage authorization of the convenient food product information corresponding to the digital menu instantiation information.

Preferably, the convenient food management server further comprises a convenient food specification information management unit which can process the convenient food specification information in the digital menu database so as to generate the convenient food specification information unit.

Preferably, the digital menu management server further comprises a digital menu information management unit which can process the digital menu information in the digital menu database so as to generate the digital menu information unit.

Preferably, the associated and corresponding relationship between the convenient food specification information and the convenient food product information is realized by embedding each of the convenient food product recognition information generated based on the convenient food specification information into the convenient food specification information unit and/or embedding the convenient food specification recognition information into each of the convenient food product information unit. The associated and corresponding relationship between the convenient food specification information and the digital menu information is realized by embedding the digital menu recognition information corresponding to the convenient food specification information into the convenient food specification information unit and/or embedding the convenient food specification recognition information corresponding to the digital menu information into the digital menu information unit. The associated and corresponding relationship between the digital menu information and the digital menu instantiation information is realized by embedding each of the digital menu instantiation recognition information generated based on the digital menu information into the digital menu information unit and/or embedding the digital menu recognition information into each of the digital menu instantiation information unit.

Preferably, the digital menu instantiation information management unit further comprises an encrypting module which performs encrypting processing on the digital menu instantiation information, especially the digital menu instantiation recognition information. That is, when the user is downloads the digital menu instantiation information, if the digital menu information is not encrypted previously, a digital encrypted processing should be performed by the digital menu management server before downloading so as to protect the rights of the producer of digital menu from being invaded illegally.

Preferably, the authorization control system further comprises an authorization request verification unit, which can respond to user's authorization request and approve the authorization verification under predetermined conditions.

The authorization control system will check the usage information on the digital menu instantiation information that was used. Typically, each digital menu instantiation information can be only allowed to be used for one time. If an abnormality is found, e.g., repeated use or multiple times of use, alarming information will be provided automatically. The authorization control system will also record the relevant information of digital menu instantiation information in the process of downloading, including the man in downloading, the date of downloading, the cause of downloading, the device used for downloading or the like, into a set of information corresponding to the digital menu instantiation information so as to track the use of digital menu instantiation information all the way.

If the digital menu instantiation information which was successfully purchased by the user is not in use and there is no need to use it, it can be returned by logging in the digital menu management server. If the digital menu management server confirms that the digital menu instantiation information was not used by searching for usage information in a set of information corresponding to the digital menu instantiation information, it deletes the digital menu instantiation information from a list of digital menu instantiation information purchased by the user. The digital menu management server can assign the digital menu instantiation information returned from the user to other users.

Optionally, as described above, the above mentioned convenient food management server and digital menu management server as well as various databases and management units built therein can be integrated in one server, one database or one management unit, e.g., a convenient food and digital menu management server, a convenient food and digital menu database, and a convenient food and digital menu management unit. Such an arrangement can also realize the effects brought about by the above system.

Figure 4:
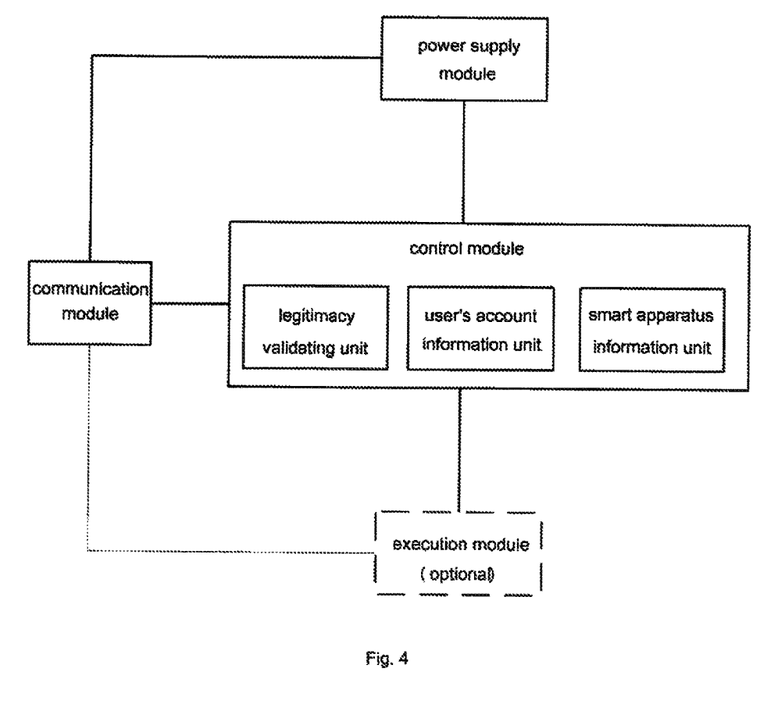
FIG. 4 is a schematic diagram showing the module components of a smart apparatus.

Based on the above authorization control method and authorization control system of convenient food and digital menu, the invention further provides a smart apparatus which can obtain a usage authorization of digital menu instantiation information corresponding to convenient food product information through the convenient food product information, or can obtain a usage authorization of convenient food product information corresponding to digital menu instantiation information through the digital menu instantiation information, while simultaneously obtaining, resolving or executing the above described digital menu instantiation information. As shown in FIG. 4, the smart apparatus comprises a control module, a communication module and a power supply module, wherein the control module is connected to the communication module, and the control module and the communication module are connected to the power supply module respectively.

Specifically, the communication module is communicatively connected to the control module for sending convenient food product information and/or digital menu information to the control module. That is, the control module downloads digital menu information from internet or server via the communication module, or the communication module communicates with a mobile portable device so as to receive digital menu information sent from the mobile portable device. The digital menu information may comprise digital menu instantiation recognition information which is obtained by processing the digital menu instantiation information. Alternatively, the control module obtains convenient food product information via the communication module, comprising for example convenient food product recognition information which is obtained by processing convenient food product information. The communication module can communicate in a wired way or wireless way. The wired communication can be one or more of conventional communication means such as Ethernet, RS232, RS485, CAN, Profibus, single bus, etc.; or can be power line carrier communication, especially power line carrier communication technology based on Homeplug technology. The wireless communication comprises one or more of communication means such as Wifi, Bluetooth, ZigBee, infrared, WiMax, GPRS, 3G, LTE or the like. In a specific embodiment, the communication module can be implemented in a form of communication chip. For example, a DM9161A chip can be used to realize Ethernet wired communication, and a CC2520 chip can be used to realize ZigBee wireless communication.

Specifically, the control module determines a correspondence between the convenient food product information and the digital menu instantiation information. Only after the information is validated legitimate, the smart apparatus can have the right to resolve and execute the digital menu instantiation information, or obtain the usage authorization of the convenient food product information corresponding to the digital menu instantiation information.

Preferably, the convenient food product information is convenient food product recognition information, and the digital menu instantiation information is digital menu instantiation recognition information. The control module determines a correspondence between the convenient food product recognition information and the digital menu instantiation recognition information. Only after the information is validated legitimate, the smart apparatus can have the right to resolve and execute the digital menu instantiation information, or obtain the usage authorization of the convenient food product information corresponding to the digital menu instantiation information. More preferably, the convenient food product recognition information and the digital menu instantiation recognition information are character code or graphic code.

In a specific embodiment, the smart apparatus can comprise a database which stores convenient food product information and digital menu instantiation information, wherein the convenient food product information comprise convenient food product recognition information, and the digital menu instantiation information comprises digital menu instantiation recognition information. Based on the information in the database, the control module can directly determine a correspondence between the convenient food product recognition information and the digital menu instantiation recognition information. Alternatively, the control module is communicatively connected to the management server via the communication module, and indirectly determine a correspondence between the convenient food product recognition information and the digital menu instantiation recognition information via the management server, wherein the management server is an integrated convenient food and digital menu management server, or a convenient food management server and a digital menu management server that are independent from each other.

Preferably, the convenient food product recognition information and the digital menu instantiation recognition information can be obtained by an indirect association with user's account information and/or smart apparatus information. When the convenient food product recognition information and the digital menu instantiation recognition information are obtained by an indirect association with user's account information and/or smart apparatus information, the control module can determine a part of all of the correspondences among the user's account information, the smart apparatus information, the convenient food product recognition information and the digital menu instantiation recognition information. If the correspondence completely fits, the smart apparatus will have the right to resolve and execute the digital menu instantiation information. For example, the user inputs the convenient food product information and the digital menu instantiation information together into the smart apparatus, which simultaneously determines a correspondence among the user's account information, the convenient food product recognition information and the digital menu instantiation recognition information based on the user's account information stored on the digital menu management server. Only if the user's account information, the convenient food product recognition information and the digital menu instantiation recognition information completely fit the correspondence, the smart apparatus can have the right to resolve and execute the digital menu instantiation information, or obtain the usage authorization of the convenient food product information corresponding to the digital menu instantiation information. In another example, the user inputs the convenient food product recognition information and the digital menu instantiation recognition information together into the smart apparatus, which simultaneously determines a correspondence among the user's account information, the smart apparatus information, the convenient food product recognition information and the digital menu instantiation recognition information based on the user's account stored on the digital menu management server and a corresponding smart apparatus information in downloading. Only if the user's account information, the smart apparatus information, the convenient food product recognition information and the digital menu instantiation recognition information completely fit the correspondence, the smart apparatus can have the right to resolve and execute the digital menu instantiation information, or obtain the usage authorization of the convenient food product information corresponding to the digital menu instantiation information.

The user's account information comprises some of all of the information of the user of downloading, the date of downloading, the device used for downloading and the software used for downloading. The smart apparatus information comprises apparatus information that can uniquely represent this smart apparatus such as smart apparatus identifying code, name, modle or technical parameter, etc., wherein the apparatus identifying code is identifying information which uniquely identifies a certain apparatus, the apparatus technical parameter can comprise information that can uniquely represent the technical ability of this smart apparatus such as cooking style, power, capacity, the number and type of ports of the apparatus as well as the type and number of sensors for status back-feeding, etc.

The smart apparatus is a universal apparatus which, after resolving the digital menu information, converts it into a control command to be transmitted to a particular smart cooking appliance for completing the cooking process of convenient food; also, the smart apparatus itself can be a functional component of the smart cooking appliance, which directly controls a corresponding functional module after resolving the digital menu information, thus completing the cooking process. Preferably, the smart apparatus can be a personal mobile terminal such as cell phone, tablet computer, etc., or can be a computer or a smart cooking appliance, etc. It can resolve the digital menu information or can operate at the same time of resolving the digital menu information, wherein the smart cooking appliance can be a kitchen appliance which can realize automatic or semi-automatic cooking such as smart electric rice cooker, smart cooking utensils, smart garnishing machine, etc.

Preferably, the digital menu information obtained by the smart apparatus can partially or entirely exist in an encrypted form. In order to process the encrypted information, the control module of the smart apparatus can also comprise a decrypting module for decrypting the encrypted information. The algorithm for encrypting and decrypting information can be a certain currently existing universal encrypting and decrypting algorithm, or can be a certain private encrypting and decrypting algorithm.

Preferably, the cooking command of digital menu information resolved by the control module of smart apparatus can be transmitted to an execution module for executing so as to convert the cooking command into a cooking process. For example, if it is required to achieve a heating ability for cooking, the execution module typically comprises at least one heating element and a control unit thereof. The smart apparatus sends a control command to the control unit of the heating element via an internal information bus. The control unit controls the heating element, and adjusts the magnitude of fire power so as to realize a heating function of the cooking process. The operation of the heating element can be based on any of existing heating manners, such as coal burning, gas burning, electric heating, infrared heating, microwave heating, ceramic heating or the like. Alternatively, for example, if a garnish automatic distributing ability is required, the smart apparatus will have to comprise a garnishing execution mechanism or a garnishing control unit which receives a garnishing command transmitted from the control module of the smart apparatus so as to drive the garnishing execution mechanism to perform a corresponding garnishing action. Alternatively, for example, if a washing ability is required in the cooking preparation process, a washing execution mechanism and a washing control unit can be added. In a specific example, the execution module can be disposed inside the smart apparatus, or can be disposed in one or more smart cooking appliances other than the smart apparatus. The execution module can be in direct communication connection with the control module via the bus, or can be in indirect communication connection via the communication module.

After the user resolves and runs the digital menu instantiation information via the smart apparatus, the relevant information during use such as user's information, date of use, used apparatus, process of use, the number of downloading and using, evaluation of use or feedback information can be firstly stored in the smart apparatus. Once the smart apparatus establishes communication connection with the digital menu management server, such information can be uploaded to the digital menu management server actively or passively, or can be directly transmitted to the digital menu management server in case of on-line. The usage information and evaluation information uploaded to the digital menu management server is stored in a corresponding set of digital menu instantiation information in the digital menu management server.

The smart apparatus can also log into the digital menu management server, and actively or passively obtains information corresponding to the digital menu information for which the smart apparatus or user's account has already obtained usage authorization on the digital menu management server. In a specific embodiment, the smart apparatus can have direct access to the management server via the communication module, or the smart apparatus can have indirect access to the management server via a certain intermediate device.

Preferably, if the smart apparatus has to send information to other devices or servers via the communication module, the information interaction between the two may also have to be encrypted. Therefore, the control module of the smart apparatus may further comprise an encrypting module. When the smart apparatus transmits information to the outside, the information is further transmitted to other devices or servers after being encrypted by the encrypting module. The information can be used normally only after being decrypted correspondingly upon receipt of the information by the other devices or servers.

Through the entire process of using the above described convenient food and digital menu, it can be seen that by creating convenient food product information and digital menu instantiation information and associating the convenient food product information and the digital menu instantiation information, an effective management of the convenient food and digital menu authorization can be realized; further, by using a corresponding set of the convenient food product information and the digital menu instantiation information, all the information in the entire flow process from generation to use of the convenient food product and uploading, releasing, purchasing, downloading and using the digital menu information can be recorded entirely. Therefore, using the above information, it is possible to track the use of the convenient food and digital menu information and prevent an illegal use of the digital menu information.

The invention claimed is:

1. An authorization control method of convenient food and a digital menu, comprising the following steps:
   (1) establishing a database on a local server which stores digital menu information, convenient food specification information corresponding to the digital menu information, one or more digital menu instantiation information generated according to the digital menu information, and one or more convenient food product information generated according to the convenient food specification information;
   (2) processing the convenient food product information and the digital menu instantiation information, respectively, on a local server so as to generate a convenient food product information unit and a digital menu instantiation information unit, respectively;
   (3) presetting on a local server corresponding digital menu instantiation information in the convenient food product information unit and/or presetting corresponding convenient food product information in the digital menu instantiation information unit;
   (4) validating on a local server information in the convenient food product information unit, and granting usage authorization of digital menu instantiation information corresponding to the convenient food product information after the information is validated as being legitimate, wherein the digital menu instantiation information comprises a sequence of executable commands to be executed by a smart cooking appliance to prepare a convenience food product for consumption; and
   (5) resolving and running the digital menu instantiation information on a smart cooking appliance and completing automatic cooking of a convenient food product by the smart cooking appliance;
   wherein automatic cooking of a convenient food product by the smart cooking appliance is an automatic process without user input.

2. The authorization control method according to claim 1, wherein processing the information comprises digitally processing the convenient food product information and the digital menu instantiation information, respectively, so as to generate convenient food product recognition information and digital menu instantiation recognition information, respectively.

3. The authorization control method according to claim 2, wherein the digital menu instantiation recognition information corresponding to the convenient food product information is built in the convenient food product information unit, and/or the convenient food product recognition information corresponding to the digital menu instantiation information is built in the digital menu instantiation information unit.

4. The authorization control method according to claim 2, wherein before step (3), the method further comprises: processing each convenient food specification information and each digital menu information in the database, respectively, so as to generate a convenient food specification information unit and a digital menu information unit, respectively; wherein processing the information comprises digitally processing the convenient food specification information and the digital menu information, respectively, so as to generate convenient food specification recognition information and digital menu recognition information, respectively.

5. The authorization control method according to claim 4, wherein each of the convenient food specification recognition information, the convenient food product recognition information, the digital menu recognition information and the digital menu instantiation recognition information are character code or graphic code depicted in machine language.

6. The authorization control method according to claim 4, wherein the convenient food specification information corresponds to and associates with the convenient food product information, the convenient food specification information corresponds to and associates with the digital menu information, and the digital menu information corresponds to and associates with the digital menu instantiation information.

7. The authorization control method according to claim 6, wherein:
   the associated and corresponding relationship between the convenient food specification information and the convenient food product information is a relationship in which one convenient food specification information corresponds to one or more convenient food product information; the associated and corresponding relationship is realized by embedding each of the convenient food product recognition information generated based on the convenient food specification information into the convenient food specification information unit and/or embedding the convenient food specification recognition information into each of the convenient food product information unit;
   the associated and corresponding relationship between the convenient food specification information and the digital menu information is realized by embedding the digital menu recognition information corresponding to the convenient food specification information into the convenient food specification information unit and/or embedding the convenient food specification recognition information corresponding to the digital menu information into the digital menu information unit; and
   the associated and corresponding relationship between the digital menu information and the digital menu instantiation information is a relationship in which one digital menu information corresponds one or more digital menu instantiation information; this associated and corresponding relationship is realized by embedding each of the digital menu instantiation recognition information generated based on the digital menu information into the digital menu information unit and/or embedding the digital menu recognition information into each of the digital menu instantiation information unit.

8. The authorization control method according to claim 1, wherein validating comprises the following process:
   obtaining the convenient food product information;
   verifying the legitimacy of the convenient food product information;
   calling out the convenient food product information unit corresponding to the convenient food product information via the convenient food product information after the convenient food product information is verified legitimate;
   obtaining use authorization of the digital menu instantiation information corresponding to the convenient food product information via the convenient food product information unit.

9. The authorization control method according to claim 8, wherein the convenient food product information is convenient food product recognition information, and the digital menu instantiation information is digital menu instantiation recognition information.

10. The authorization control method according to claim 9, wherein the convenient food product information or the digital menu instantiation information is a character code or graphic code depicted in encrypted machine language.

11. The authorization control method according to claim 1, wherein the use authorization of the digital menu instantiation information comprises partial or entire limitations on the times of downloading/using, the scope of downloading/using and the term of downloading/using the digital menu instantiation information.

12. The authorization control method according to claim 1, wherein the digital menu instantiation information and the convenient food product information are generated automatically or generated upon a user's request.

* * * * *